United States Patent [19]
Adamczyk et al.

[11] Patent Number: 5,413,911
[45] Date of Patent: May 9, 1995

[54] DETERMINATION OF TRICYCLIC ANTIDEPRESSANT DRUGS IN THE PRESENCE OF INTERFERING SUBSTANCES

[75] Inventors: Maciej Adamczyk, Gurnee; Jeffrey R. Fishpaugh, Chicago; Charles A. Harrington, Lake Villa; Daryl E. Hartter, Mundelein; Robert E. Hruska, Libertyville, all of Ill.

[73] Assignee: Abbott Laboratories, Abbott Park, Ill.

[21] Appl. No.: 627,282

[22] Filed: Dec. 14, 1990

[51] Int. Cl.$^6$ ..................... G01N 33/53; G01N 30/02
[52] U.S. Cl. .................................. 435/7.1; 435/7.92; 436/96; 436/91; 436/119; 436/537; 422/70
[58] Field of Search ................ 435/7.1, 7.92, 962, 435/973; 436/537, 73, 74, 911, 96, 119, 120, 825; 422/70

[56] References Cited

U.S. PATENT DOCUMENTS

| | | | |
|---|---|---|---|
| 4,668,620 | 5/1987 | Armenta et al. | 436/825 X |
| 4,810,635 | 3/1989 | Ledden et al. | 436/825 X |
| 4,820,416 | 4/1989 | Chang et al. | 210/632 |
| 4,829,012 | 5/1989 | Cambiaso et al. | 436/512 |
| 4,886,743 | 12/1989 | Hood et al. | 435/5 |
| 5,216,132 | 6/1993 | Basi | 530/387.3 |

FOREIGN PATENT DOCUMENTS

| | | | |
|---|---|---|---|
| 0411604A3 | 8/1990 | European Pat. Off. | 435/28 X |
| WO90/07115 | 6/1990 | WIPO | 435/28 X |

OTHER PUBLICATIONS

Burns et al., "Both Rat and Mouse T Cell Receptors Specific for the Encephalitogenic Determinant of Myelin Basic Protein Use Similar V α and V β Chain Genes Even Though the Major Histocompatibility Complex and Encephalitogenic Determinants Being Recognized are Different", J. Exp. Med., 169:27–39 (1989).

Urban et al., "Restricted use of T Cell Receptor V Genes in Murine Autoimmune Encephalomyelitis Raises Possibilities for Antibody Therapy", Cell, 54:577–592 (1988).

Lohse et al., "Control of Experimental Autoimmune Encephalomyelitis by T Cells Responding to Activated T Cells", Science, 244:820–822 (1989).

Banerjee et al., "Possible Role of V$_\beta$ T Cell Receptor Genes in Susceptibility to Collagen-Induced Arthritis in Mice", J. Exp. Med., 167:832–839 (1988).

Fowlkes et al., "A Novel Population of T-cell Receptor αβ-Bearing Thymocytes Which Predominantly Expresses a Single V$_\beta$ Gene Family", Nature, 329:251–254 (1987).

Shortman et al., "Mouse Strain Differences in Subset Distribution and T Cell Antigen Receptor Expression Among CD4−CD8−Thymocytes", Immunol. Cell Biol., 66:423–433 (1988).

Takahama et al., "Phenotype, Ontogeny, and Repertoire of CD4−CD8−T Cell Receptor αβ+ Thymocytes", J. Immunol., 146:1134–1141 (1991).

(List continued on next page.)

*Primary Examiner*—Carol A. Spiegel
*Attorney, Agent, or Firm*—Gregory W. Steele

[57] ABSTRACT

Method and reagents for determining a compound of interest present in a test sample also containing one or more interfering compounds having substantially similar chemical structures, and otherwise analytically indistinguishable from each other, employing a pretreatment reagent capable of selectively modifying the chemical structure of one of the compounds without significantly modifying or altering the chemical structure of the other one of the compounds. The selective modification results in the modified compound having a chemical structure which is substantially dissimilar to the chemical structure of the other one of said compounds wherein the compounds are substantially distinguishable from each other to permit the analytical determination of one or the other of such compounds by immunoassay, high pressure liquid chromatography, and thin layer chromatography techniques, especially for the fluorescent polarization immunoassay determination of tricyclic antidepressant drugs in the presence of phenothiazines.

14 Claims, No Drawings

OTHER PUBLICATIONS

Bertness et al., "T-Cell Receptor Gene Rearrangements as Clinical Markers of Human T-Cell Lymphomas", N. Engl. J. Med., 313:534–538 (1985).

Tomai et al., "Superantigenicity of Streptococcal M Protein", J. Exp. Med., 172:359–362 (1990).

Atkin et al., "Stimulation of Mouse Lymphocytes by a Mitogen Derived from Mycoplasma Arthritidis", J. Immunol., 137:1581–1589 (1986).

Cole and Ward, "Mycoplasmas as Arthritogenic Agents", In: The Mycoplasmas, vol. IV, New York, Academic Press, pp. 367–398 (1979).

Cole et al., "Stimulation of Mouse Lymphocytes by a Mitogen Derived From Mycoplasma arthritidis", J. Immunol., 142:4131–4137 (1989).

Chothia et al., "The Outline Structure of the T-Cell $\alpha\beta$ Receptor", EMBO J., 7:3745–3755 (1988).

Howell et al., "Clonal Infiltrates of Activated V$\beta$17+T Cells in Synovial Tissues of Rheumatoid Arthritis Patients", J. Cell Biochem. Suppl., 15A:295 (1991).

Pallard et al., "Evidence for the Effects of a Superantigen in Rheumatoid Arthritis", Science, 253:325–329 (1991).

Towbin et al., "Electrophoretic Transfer of Proteins from Polyacrylamide Gels to Nitrocellulose Sheets: Procedure and Some Applications", Proc. Natl. Acad. Sci. USA, 76:4350–4354 (1979).

Wang et al., "Stimulation and Expansion of a Human T-Cell Subpopulation by a Monoclonal Antibody to T-Cell Receptor Molecule", Hybridoma, 5:719–790 (1986).

Posnett et al., "Inherited Polymorphism of the Human T-Cell Antigen Receptor Detected by a Monoclonal Antibody", Proc. Natl. Acad. Sci. USA, 83:7888–7892 (11986).

Li et al., "Allelic Variations in the Human T Cell Receptor V$\beta$6.7 Gene Products", J. Exp. Med., 171:221–230 (1990).

Friedman et al., "Amplification of Altered Self-reactive Cytolytic T Lymphocyte Responses by Cloned, Allospecific Human $T_h$ Cells", J. Clin. Invest., 82:1722–1730 (1988).

Choi et al., "Selective Expansion of T Cells Expressing V$\beta$2 in Toxic Shock Syndrome", J. Exp. Med., 172:981–984 (1990).

Fleischer et al., "An Evolutionary Conserved Mechanism of T Cell Activation by Microbial Toxins", J. Immunol., 146:11–17 (1991).

Posnett et al., "A Novel Method for Producing Anti-peptide Antibodies", J. Biol. Chem., 263:1719–1725 (1988).

Chomczynski and Sacchi, "Single-Step Method of RNA Isolation by Acid Guanidinium Thiocyanate–Phenol–Chloroform Extraction", Anal. Biochem., 162:156–159 (1987).

Concannon et al., "Diversity and Structure of Human T-Cell Receptor $\beta$-Chain Variable Region Genes", Proc. Natl. Acad. Sci. USA, 83:6598–6602 (1986).

Kimura et al., "Sequences and Repertoire of the Human T Cell Receptor $\alpha$ and $\beta$ Chain Variable Region Genes in Thymocytes", Eur. J. Immunol., 17:375–383 (1987).

Aldrich Chemical Catalog 1986, pp. 283, 1194 and 1196.

Alltech Chromatography Catalog 1988, pp. 58, 258–264.

Chemical Abstract 98 (7):46295.

Chemical Abstract 106(17):31135.

Biosis Abstract 68056243.

DETERMINATION OF TRICYCLIC ANTIDEPRESSANT DRUGS IN THE PRESENCE OF INTERFERING SUBSTANCES

FIELD OF THE INVENTION

The present invention relates to the determination of analytes in a test sample also containing one or more analytically interfering substances. In particular, the present invention relates to the pretreatment of a test sample to permit the analytical determination of an analyte in the presence of one or more interfering substances, especially for the determination of tricyclic antidepressant drugs.

BACKGROUND OF THE INVENTION

The determination of analytes has become very useful in a variety of fields such as biochemical research, environmental and industrial testing, and especially medical diagnostics. The monitoring of therapeutic drug levels and other analytes in biological fluids such as serum, plasma, whole blood, urine, and the like, has become very useful to provide physicians with information to aid in patient management. The monitoring of such drug levels enables adjustment of patient dosage to achieve optimal therapeutic effects, and helps avoid either subtherapeutic or toxic levels.

A test sample may contain one or more detectable compounds having chemical structures which are substantially similar to, or which resemble, or which could resemble, and therefore be indistinguishable from, the desired analyte of interest. For example, in the area of medical diagnostics where it is important to monitor the level of therapeutic drugs, a number of drugs having substantially similar chemical structures may be administered to a patient wherein a test sample from such patient could contain detectable levels thereof.

In such instances, the analytical determination of the desired analyte may be interfered with by the presence of such one or more additional substances having substantially similar chemical structures to the chemical structure of the analyte of interest to thereby produce inconsistent and inaccurate results. In particular, where the analytical determination involves immunoassay techniques employing antibodies capable of binding to the analyte of interest, such antibodies may also bind or crossreact with such other substances having substantially similar chemical structures. Similarly, where the analytical determination involves high pressure liquid chromatography techniques or thin layer chromatography techniques, the elution profile of the analyte of interest may be indistinguishable from the elution profile of such other substances having substantially similar chemical structures.

SUMMARY OF THE INVENTION

The present invention relates to the discovery that analytical systems for the determination of one or more compounds of interest present in a test sample also containing one or more compounds having substantially similar chemical structures to the one or more compounds of interest, and otherwise analytically difficult to distinguish from each other, can be greatly improved by employing a pretreatment reagent according to the present invention. In particular, the pretreatment reagent is capable of selectively modifying the chemical structure of one or more of the interfering substances without significantly modifying or altering the chemical structure of such compounds of interest. According to the present invention, the test sample is contacted with the pretreatment reagent which results in the modification of such interfering substances present in the test sample yielding substances having chemical structures which are substantially dissimilar to the chemical structure of the desired compound wherein such compounds become substantially distinguishable from each other to permit the analytical determination of one or the other of such compounds by, for example, immunoassay, high pressure liquid chromatography, or thin layer chromatography techniques. Accordingly, by chemically modifying one of such compounds as described by the present invention, methods previously required to permit the selective detection of an analyte of interest in the presence of other substances which interfere with the detection of the analyte of interest are no longer necessary.

According to a preferred embodiment of the present invention, the pretreatment reagent is an oxidative reagent which is useful for the derivatization of sulfur-containing compounds which may be present in a test sample, particularly for the fluorescent polarization immunoassay determination of tricyclic antidepressant drugs in the presence of phenothiazines. As would be understood by one skilled in the art, phenothiazines are often co-prescribed to a patient being treated with a tricyclic antidepressant drug wherein a test sample from such patient would therefore contain levels of both drugs. According to such preferred embodiment, such test sample is contacted with an oxidative reagent, preferably chloramine-T (sodium salt of N-chloro-4-methylbenzene sulfonamide) or chloramine-B (sodium salt of N-chlorobenzene sulfonamide), to selectively modify the chemical structure of the phenothiazines whereby the phenothiazines present in the test sample are selectively oxidized to their corresponding sulfoxides or sulfones. After such pretreatment of the test sample, determination of the tricyclic antidepressant drug can be accomplished, for example, according to immunoassay techniques known in the art, preferably fluorescent polarization immunoassay techniques and enzyme immunoassay techniques, wherein crossreactivity of the modified phenothiazine with the antibody to the tricyclic antidepressant drug is substantially reduced.

DETAILED DESCRIPTION OF THE INVENTION

The present invention is particularly useful for the determination of an analyte of interest present in a test sample also containing one or more interfering substances having substantially similar chemical structures to, or chemical structures which resemble or could resemble, the analyte of interest. It is to be understood that the analyte of interest and such interfering substances could be substantially dissimilar but, at the same time, could have conformational aspects in which they resemble each other.

In particular, analytes of interest and interfering substances include, but are not intended to be limited to, tricyclic antidepressant drugs such as amitriptyline, nortriptyline, imipramine, desipramine, protriptyline, doxepin, clomipramine, desdoxepin, and the like; phenothiazines such as chlorpromazine, desmethylchlorpromazine, thioridazine, desmethylthioridazine, sulforidazine, mesoridazine, and the like; and benzodiazepines such as diazepam and the like; thioxanthines such as thiothixene and the like.

According to the present invention, the pretreatment reagent is specific for and is capable of selectively modifying the chemical structure at one or more sites or positions of one or more analytes or interfering substances present in a test sample. It is to be appreciated that although modification of the chemical structure of the interfering substance is preferred, the chemical structure of the analyte of interest can also be modified without departing from the teachings of the present invention. It is also to be appreciated that once the chemical structure of either the analyte of interest or the interfering substance has been modified according to the present invention, the analytical determination of the one or the other can be made. Also according to the present invention, the pretreatment reagent can be selected from a variety of reagents capable of substantially modifying the chemical structure of either the analyte of interest or the interfering substance. Such reagents include, but are not intended to be limited to, oxidative reagents, particularly N-chlorosulfonamides such as chloramine-T, chloramine-B, and the like; hypochlorites such as sodium hypochlorite, hypochlorous acid, and the like; hypobromites such as sodium hypobromite, hypobromous acid, and the like; peroxides such as sodium hydroperoxide and the like; peracids such as perselenic acid, 3-chloroperbenzoic acid, and the like; and oxidative enzymes such as catalase, peroxidase, microperoxidase, and the like. For tricyclic antidepressant drugs in the presence of other sulfur-containing substances, such as phenothiazines, the pretreatment reagent is preferably an oxidative reagent selected from the group consisting of sodium hypochlorite, catalase, and perselenic acid, more preferably chloramine-T.

As would be understood by one skilled in the art apprised of the foregoing considerations and as will be described in greater detail in the specific embodiments and examples hereinbelow, selection of a particular pretreatment reagent will depend upon the chemical structure of the analyte of interest and the chemical structure of interfering substances which may be present in a test sample. It is to be understood that in addition to being added or introduced into a test sample from an external source, the oxidative reagent can alternatively be generated or otherwise formed in situ, such as the generation of hydrogen peroxide. For example, in the case of an analytical system containing the analyte of interest, an interfering substance as described herein, selenium dioxide, and glucose oxidase, to which glucose is added, hydrogen peroxide is formed in situ. This is particularly useful for the packaging of reagents in that the packaging and shipment of strong oxidizing agents can be avoided by providing reagents which can form, in situ, the oxidative reagent for use as described herein. In addition, the pretreatment reagent can be presented as a liquid reagent, a dry reagent, or immobilized to a solid support material according to methods known in the art.

Although the pretreatment reagent can be employed in various analytical systems as described above, the pretreatment reagent according to the present invention is especially useful in an immunoassay system. For example, in a competitive protein binding or immunoassay, a substance being measured, often referred to as a ligand, competes with a substance of close structural similarity coupled to a detectable moiety, often referred to as a tracer, for a limited number of binding sites on antibodies specific to the portion or portions of the ligand and tracer with structural similarity, shared with an immunogen employed to produce such antibodies. In a fluorescent polarization immunoassay (FPIA), the detectable moiety component of the tracer is a fluorescent moiety selected from the group consisting of fluoresceins, aminofluoresceins, carboxyfluoresceins, fluoresceinamines, and the like.

According to such FPIA format, which is particularly preferred according to the present invention, the amount of tracer bound to the antibody varies inversely to the amount of ligand present in either the test sample or standard calibrator solution in a predictable manner. The relative, and therefore characteristic, binding affinities of the ligand and the tracer to the antibody binding site, are important parameters of the assay system. In particular, FPIA techniques are based on the principle that a fluorescent tracer, when excited by plane polarized light of a characteristic wavelength, will emit light at another characteristic wavelength (i.e., fluorescence) that retains a degree of the polarization relative to the incident stimulating light that is inversely related to the rate of rotation of the tracer in a given medium. As a consequence of this property, a tracer substance with constrained rotation, such as in a viscous solution phase or when bound to another solution component with a relatively lower rate of rotation, will retain a relatively greater degree of polarization of emitted light than if in free solution. Therefore, within the time frame in which the ligand and tracer compete for binding to the antibody, the tracer and ligand binding rates should yield an appropriate proportion of free and bound tracer with the preservation of important performance parameters such as selectivity, sensitivity, and precision.

For example, for the FPIA determination of imipramine, a test sample is contacted with the pretreatment reagent according to the present invention and with imipramine antiserum in the presence of an appropriately selected fluorescein derivative thereof which is capable of producing a detectable fluorescence polarization response to the presence of imipramine antiserum. Plane polarized light is then passed through the solution to obtain a fluorescent polarization response and the response is detected as a measure of the amount of imipramine present in the test sample when compared to the response of standard calibrators prepared from the native compound.

As described herein, the test sample containing the analyte of interest and such other interfering substances can be a naturally occurring or artificially formed liquid, and includes, but is not intended to be limited to biological test samples such as whole blood, serum, plasma, urine, feces, saliva, cerebrospinal fluid, brain tissue, and the like, and industrial and environmental test samples such as soil, sewage, water, vehicular emissions, fossil fuels, and the like. In addition, the test sample can be an extract of a test sample, or any derivative thereof. For example, the test sample can be one which is subjected to chromatographic fractionation, in which the above-described oxidative pretreatment is carried out prior to, during, or subsequent to such fractionation, or on any or all fractions.

It is to be appreciated that the scope of the invention is not intended to be limited to the analytical techniques described herein, and that the method of the present invention can be employed in a variety of analytical techniques which require distinguishing characteristics between two or more compounds as described herein in order to make such determination.

A test kit according to the present invention comprises a pretreatment reagent as described above and all of the essential reagents required to perform a desired analytical determination as described herein. The test kit is presented in a commercially packaged form as a combination of one or more containers holding the necessary reagents, as a composition or admixture where the compatibility of the reagents will allow. Particularly preferred is a test kit for the fluorescent polarization immunoassay determination of tricyclic antidepressant drugs, comprising the appropriate pretreatment reagent according to the present invention, an appropriate fluorescent tracer compound, and an appropriate antibody reagent as described above. It is to be understood that the test kit can, of course, include other materials as are known in the art and which may be desirable from a commercial user standpoint, such as buffers, diluents, standards, and the like.

The present invention will now be illustrated, but is not intended to be limited, by the following examples:

EXAMPLE 1

Fluorescent Polarization Immunoassay For Imipramine and Desipramine

In a fluorescent polarization immunoassay (FPIA) using an Abbott TDx ® analytical system for imipramine (IMI) or desipramine (DMI), phenothiazines such as chlorpromazine may interfere with the determination of IMI and DMI. In particular, antibodies directed to IMI may recognize chlorpromazine or desmethylchlorpromazine as well as imipramine when present in a patient sample. In order to prevent the error in quantitation that would result, the sample is treated with chloramine-T to oxidatively modify the structure of the chlorpromazine or desmethylchlorpromazine to a form much less well recognized by this antitricyclic immune serum.

For the determination of imipramine, the sample (0.100 mL) was rendered basic by the addition of 0.100 mL of 0.25M NaOH and dissociated from serum proteins by the addition of 0.025 mL of isoamyl alcohol. The mixture was allowed to stand for up to 5.0 minutes, after which time 0.50 mL of decane was added and the sample vortexed vigorously for 1.0 minute. The sample/decane biphasic mixture was then centrifuged for up to 5.0 minutes to clarify those phases. In the case of imipramine, 0.100 mL of the decane upper phase was transferred to a tube containing 0.100 mL of acidic buffer, pH 3, to which 0.010 mL of 20 microgram per mL of chloramine-T had been added. This amount of chloramine-T can completely modify up to 1.0 microgram of chlorpromazine in the original sample. Variations in the quantity of chloramine-T may be made to accommodate differing ranges of phenothiazine concentrations expected to be present in the sample. Table I below illustrates a typical example of results obtained from comparing the analysis of a sample containing, as in this case, 300 ng/mL of chlorpromazine and 128 ng/mL of imipramine, employing an Abbott TDx analytical system. Chlorpromazine crossreacts with the antibody used in the FPIA for imipramine. This quantity of chlorpromazine yielded a significant overestimate of the amount of imipramine actually present in the sample (171%). Treatment of the sample extract with chloramine-T modifies the structure of the chlorpromazine in such a fashion that it is no longer an assay interferant. Inclusion of the chloramine-T treatment removed this overestimate entirely.

TABLE I

Removal Of Chlorpromazine Interferant In FPIA For Imipramine

| Sample | Treatment | Mass |
| --- | --- | --- |
| IMI | NONE | 128 ng/mL |
| IMI + 300 ng CPZ | NONE | 219 ng/mL |
| IMI + 300 ng CPZ | Chloramine-T | 130 ng/mL |

The procedured described above could also be followed for the analysis of desipramine in the presence of phenothiazines to achieve the elimination of interfering substances as described herein.

EXAMPLE 2

High Pressure Liquid Chromatography Determination of Imipramine and Desipramine

In the HPLC analysis of tricyclic antidepressants such as imipramine and desipramine, phenothiazines such as chlorpromazine or its metabolite, desmethylchlorpromazine, may interfere with the analysis of the tricyclic antidepressants or one of their metabolites.

A 1.0 mL sample to which an internal standard substance was added was rendered basic by the addition of 0.200 mL of 1.0M NaOH followed by the addition of 0.200 mL of isoamyl alcohol to inhibit analyte/protein interaction. Ten mL of heptane was then added and the biphasic mixture shaken for 1.0 hour followed by 30 minutes of centrifugation at about $2000 \times g$. The heptane layer was then transferred in its entirety to a test tube containing 1.0 mL of an acidic buffer, pH 3, to which 0.100 mL of 100 micrograms/mL chloramine-T had been added. The acidic buffer was then made basic by the addition of 0.200 mL of 1M NaOH followed by 0.100 mL of isoamyl alcohol. To this solution, 5.0 mL of pentane was added and the biphasic mixture was shaken for 30 minutes followed by centrifugation at about $2000 \times g$. The pentane was pipetted into a small vial, reduced to dryness with a stream of nitrogen and reconstituted in HPLC mobile phase. An aliquot was then analyzed by HPLC utilizing a spectrophotometric ultraviolet detector. Compounds of interest in this case were quantified by observation at 254 nm.

HPLC analysis may be accomplished with many different mobile phases. The example utilized a 3 micron silica stationary phase in a column of 6 mm×15 cm. The mobile phase consisted of a mixture of 80 parts of 25 mM $NaH_2PO_4$, pH 3.0, 20 parts of acetonitrile, and was doped with 21 mM n-nonylamine. The column exhibited approximately 150,000 theoretical plates per meter in a test system used by the manufacturer. Treatment with chloramine-T completely eliminated the desmethylchlorpromazine as an interfering substance.

EXAMPLE 3

Fluorescent Polarization Immunoassay For Total Doxepins In The Presence Of Phenothiazines The present example illustrates that chlorpromazine (CPZ) is significantly recognized in the immunoassay for doxepin and desdoxepin (Total DOX) and gives incorrect readings for the quantitation of Total DOX (Table II). These data also show that including chloramine-T in the procedure removes the recognition of CPZ in the immunoassay for Total DOX.

To a 0.25 mL solution containing Total DOX and CPZ was added 0.90 mL of heptane:isoamyl alcohol (35:1, v/v) solution and 0.100 mL of sodium carbonate solution. After vortexing for 60 seconds and centrifuging for 30 seconds, 0.50 mL of the upper phase (heptane:isoamyl alcohol phase) was transferred to a clean tube. Next, 0.100 mL of HCl (0.05N) and 0.040 mL of either distilled water or chloramine-T (0.040 mg/mL) in distilled water were added. After vortexing for 30 seconds, waiting 120 seconds, and centrifuging for 30 seconds, 0.085 mL of the lower phase (aqueous phase of HCl and water with or without chloramine-T) was transferred for quantitation by immunoassay for Total DOX employing an Abbott TDx analytical system.

In a sample containing Total DOX at 100 ng/mL and CPZ at 1000 ng/mL, the concentration in the immunoassay without the addition of chloramine-T was 232 ng/mL or an error of more than twofold as shown in Table II below. The addition of chloramine-T removed the recognition of CPZ by the immunoassay for Total DOX and a value of 95 ng/mL was obtained. This procedure allows quantitation of Total DOX by immunoassay in samples containing CPZ.

TABLE II

Removal of Chlorpromazine Interferant In Abbott TDx Total DOX FPIA

| Amount Total DOX Added | Amount CPZ Added | Concentration of Total DOX when the procedure includes: | |
|---|---|---|---|
| | | Water | Chloramine-T |
| 0 | 1000 | 143 | 7 |
| 0 | 2000 | 197 | 10 |
| 50 | 1000 | 181 | 49 |
| 75 | 1000 | 199 | 83 |
| 100 | 1000 | 232 | 95 |
| 100 | 0 | 104 | 101 |
| 125 | 500 | 223 | 135 |
| 150 | 1000 | 274 | 155 |
| [all concentrations in ng/mL] | | | |

EXAMPLE 4

Fluorescent Polarization Immunoassay For Amitriptyline and Nortriptyline

Chlorpromazine (CPZ) crossreacts with the antibodies used in the FPIA determinations of amitriptyline (AMI) and nortriptyline (NOR), which lead to significant overestimations of AMI and NOR levels. Treatment of a test sample with chloramine-T according to the present invention modifies oxidatively the structure of chlorpromazine in such a fashion that it no longer crossreacts in either immunoassay.

A test sample (0.200 mL) was made basic by the addition of 0.050 mL of 1N NaOH and dissociated from serum proteins by addition of 0.050 mL isoamyl alcohol; this mixture was briefly mixed and allowed to stand for at least 5.0 minutes, after which time 0.500 mL of n-heptane was added and the sample vortexed vigorously for 30 seconds. The sample/n-heptane biphasic mixture was centrifuged at 10,000×g for 1 minute to clarify the phases. A measured 0.400 mL aliquot of the upper (n-heptane) phase was then transferred to a new tube with 0.400 mL of 0.1M glycyl-glycine buffer (pH 3) and vortexed vigorously for 30 sec. Forty microliters (0.040 mL) of chloramine-T solution (100 ug/mL) was then added to the biphasic mixture (chloramine-T treatment as shown in Table III); in the control condition (no treatment), 0.040 mL of extraction buffer was added in place of chloramine-T. Samples were centrifuged at 10,000×g for 1 minute, with the bottom (glycyl-glycine) phase taken for analysis. Treated and untreated samples were run in duplicate on the Abbott TDx analytical system, and concentrations were determined using stored calibration curves for either AMI or NOR.

TABLE III

Removal of Chlorpromazine Interferant In Abbott TDx Amitriptyline and Nortriptyline FPIA

| SAMPLE | TREATMENT | CONCENTRATION |
|---|---|---|
| AMI | NONE | 75 ng/mL |
| AMI + CPZ | NONE | 300 ng/mL |
| AMI + CPZ | Chloramine-T | 78 ng/mL |
| NOR | NONE | 65 ng/mL |
| NOR + CPZ | NONE | 101 ng/mL |
| NOR + CPZ | Chloramine-T | 73 ng/mL |
| [CPZ concentration = 1,000 ng/mL] | | |

Accordingly, treatment with chloramine-T allowed for the correct determination of AMI and NOR levels in the presence of high concentrations of chlorpromazine.

EXAMPLE 5

High Pressure Liquid Chromatography Determination of Amitriptyline and Nortriptyline In the HPLC analysis of tricyclic antidepressants such as amitriptyline and nortriptyline, phenothiazine drugs such as chlorpromazine or its metabolite desmethylchlorpromazine may interfere with analysis of these antidepressant drugs or their hydroxylated metabolites. Individual 0.400 mL aliquots containing nortriptyline, 10-hydroxyamitriptyline, amitriptyline, desmethylchlorpromazine, and chlorpromazine were treated with either 0.040 mL of chloramine-T solution (100 ug/mL) or 0.040 mL of water. In each instance, the total sample (0.440 mL) was made basic by the addition of 0.050 mL of 1N sodium hydroxide, and 1.0 mL of n-pentane was then added. The biphasic mixture was vortexed vigorously for 1 minute and centrifuged at 10,000×g for 1 minute. The pentane layer was transferred in its entirety to a conical test tube, reduced to dryness with a stream of nitrogen and reconstituted in HPLC mobile phase. An aliquot was then analyzed by HPLC using spectrophotometric ultraviolet detection at 254 nm. The solid- and mobile-phase constituents for this HPLC analytical procedure were as described in Example 2 above.

EXAMPLE 6

Removal of Chlorpromazine Interferant By Selenium Dioxide In The Presence of Hydrogen Peroxide A test sample (0.100 mL) containing imipramine was rendered basic by the addition of 0.100 mL of 0.25M NaOH and dissociated from serum proteins by the addition of 0.025 mL of isoamyl alcohol. The mixture was allowed to stand for up to 5.0 minutes, after which time 0.50 mL of nonane was added and the sample vortexed vigorously for 1.0 minute. The mixture was then centrifuged for up to 5.0 minutes at approximately 2000×g to clarify the phases. A 0.100 mL aliquot of the nonane upper phase was then transferred to a tube containing 0.100 mL of an acidic buffer containing 100 ug/mL of selenium dioxide ($SeO_2$). To this biphasic mixture, 20 uL of a 30% aqueous solution of $H_2O_2$ was added and the mixture was vortexed, ninety microliters (0.090 mL) of the lower aqueous phase was then transferred to the sample wells and analyzed by the Abbott TDx analytical system (Table IV). Treatment of the sample extract with selenium dioxide and hydrogen peroxide modified the chemical structure of chlorpromazine such that it was no longer an assay interferant whereas selenium dioxide in the absence of hydrogen peroxide did not cause the conversion of chlorpromazine to chlorpromazine sulfoxide or sulfone.

TABLE IV

Removal Of Chlorpromazine Interferant In FPIA For Imipramine

| Sample | Treatment | Mass Measured |
| --- | --- | --- |
| IMI | NONE | 15 ng/mL |
| IMI + 312 ng CPZ | NONE | 98 ng/mL |
| IMI + 312 ng CPZ | $SeO_2 + H_2O_2$ | 14.7 ng/mL |

It will be apparent that many modifications and variations of the present invention as herein set forth are possible without departing from the spirit and scope hereof, and that, accordingly, such limitations are imposed only as indicated by the appended claims.

We claim:

1. An immunoassay method for determining the amount of a tricyclic antidepressant drug in a biological test sample, wherein said tricyclic antidepressant drug does not contain a sulfur moiety and wherein said biological test sample contains a sulfur-containing compound having a chemical structure which is similar to said tricylic antidepressant drug and is immunologically crossreactive with an antibody capable of specifically binding to said tricyclic antidepressant drug or an analogue thereof, said method comprising the steps of:

(a) forming a pretreatment solution by contacting said biological test sample with an oxidative reagent which modifies the chemical structure of said sulfur-containing compound by selectively oxidizing the sulfur moiety of said sulfur-containing compound without modifying the chemical structure of said tricyclic antidepressant drug, whereby crossreactive binding of said antibody to said modified sulfur-containing compound is substantially reduced;

(b) contacting said pretreatment solution with (i) a labeled reagent comprising said tricyclic antidepressant drug or analogue thereof labeled with a fluorescent moiety, and (ii) said antibody to form a reaction solution wherein said labeled reagent produces a measurable fluorescence polarization response when specifically bound to said antibody;

(c) measuring the fluorescent polarization response; and, (d) correlating the measured fluorescent polarization response to the amount of said tricyclic antidepressant drug present in said biological test sample.

2. The method of claim 1 wherein said biological test sample is selected from the group consisting of whole blood, urine, serum, plasma, cerebrospinal fluid and saliva.

3. The method of claim 1 wherein said oxidative reagent is generated in situ.

4. The method of claim 1 wherein said oxidative reagent is selected from the group consisting of N-chlorosulfonamides, hypochlorites, hypobromites, peroxides, peracids, and oxidase enzymes.

5. The method of claim 1 wherein said oxidative reagent is a sodium salt of N-chloro-4-methylbenzene sulfonamide.

6. The method of claim 1 wherein said tricyclic antidepressant drug is selected from the group consisting of amitriptyline, nortriptyline, imipramine, desipramine, protriptyline, doxepin, desdoxepin, and clomipramine.

7. The method of claim 1 wherein said sulfur-containing substance is a phenothiazine selected from the group consisting of chlorpromazine, desmethylchlorpromazine, thioridazine, desmethylthioridazine, sulforidazine, and mesoridazine.

8. A high pressure liquid chromatography (HPLC) method for determining the amount of a tricyclic antidepressant drug in a biological test sample, wherein said tricyclic antidepressant drug does not contain a sulfur moiety and wherein said biological test sample comprises a sulfur-containing compound having a chemical structure and elution profile similar to the chemical structure and elution profile of said tricyclic antidepressant drug, said method comprising the steps of:

(a) forming an admixture of an aliquot of said biological test sample and an internal standard;

(b) forming a pretreatment solution by contacting said admixture with an oxidative reagent which modifies the chemical structure of said sulfur-containing compound by selectively oxidizing the sulfur moiety of said sulfur-containing compound without modifying the chemical structure of said tricyclic antidepessant drug, whereby the elution profile of said modified sulfur-containing compound is substantially different from the elution profile of said tricyclic antidepressant drug;

(c) contacting said pretreatment solution to an HPLC stationary phase and eluting therefrom with a mobile phase; and, (d) measuring elution times and absorbances of said internal standard and said tricyclic antidepressant drug as they elute from the stationary phase in order to determine the amount of said tricyclic antidepressant drug in said biological test sample.

9. The method of claim 8 wherein said biological test sample is selected from the group consisting of whole blood, urine, serum, plasma, cerebrospinal fluid and saliva.

10. The method of claim 8 wherein said oxidative reagent is a peroxide generated in situ.

11. The method of claim 9 wherein said oxidative reagent is selected from the group consisting of N-chlorosulfonamides, hypochlorites, hypobromites, peroxides, peracids, and oxidase enzymes.

12. The method of claim 8 wherein said oxidative reagent is a sodium salt of N-chloro-4-methylbenzene sulfonamide.

13. The method of claim 8 wherein said tricyclic antidepressant drug is selected from the group consisting of amitriptyline, nortriptyline, imipramine, desipramine, protriptyline, doxepin, desdoxepin, clomipramine and desmethylclomipramine.

14. The method of claim 8 wherein said sulfur-containing substance is a phenothiazine selected from the group consisting of chlorpromazine, desmethylchlorpromazine, thioridazine, desmethylthioridazine, sulforidazine, and mesoridazine.

* * * * *

UNITED STATES PATENT AND TRADEMARK OFFICE
CERTIFICATE OF CORRECTION

PATENT NO. : 5,413,911
DATED : May 9, 1995
INVENTOR(S) : M. Adamczyk, J. Fishpaugh, C. Harrington, D. Hartter, R. Hruska It is certified that error appears in the above-indentified patent and that said Letters Patent is hereby corrected as shown below:

Column 10, line 30, change "antidepessant" to --antidepressant--.

Signed and Sealed this

Nineteenth Day of September, 1995

Attest:

BRUCE LEHMAN

Attesting Officer

Commissioner of Patents and Trademarks